US00PP08216P

United States Patent [19]

Van Der Knaap

[11] Patent Number: Plant 8,216

[45] Date of Patent: Apr. 27, 1993

[54] CHRYSANTHEMUM PLANT NAMED DEFINITE EYES

[75] Inventor: Jack Van Der Knaap, AX De Lier, Netherlands

[73] Assignee: Fides Beheer B.V., De Lier, Netherlands

[21] Appl. No.: 712,086

[22] Filed: Jun. 7, 1991

[51] Int. Cl.[5] ..... A01H 5/00

[52] U.S. Cl. ..... Plt./74.1

[58] Field of Search ..... Plt./74.1, 82.1, 82.4

[56] References Cited

U.S. PATENT DOCUMENTS

P.P. 4,629 1/1981 Jessel, Jr. et al. ..... Plt. 74
P.P. 5,738 5/1986 Duffett ..... Plt. 74
P.P. 6,302 9/1988 van der Knaap ..... Plt. 74
P.P. 6,851 6/1989 van Wingerden ..... Plt. 74

*Primary Examiner*—Howard J. Locker
*Attorney, Agent, or Firm*—Burns, Doane, Swecker & Mathis

[57] ABSTRACT

A new and distinct variety of Chrysanthemum plant. The new plant is characterized by its flat capitulum form, anemone capitulum type, pinkish white ray floret color, darker purple contrasting disc floret color, a diameter across face of capitulum of 4.0–7.0 cm, upright to spreading branching pattern with ca. 3–5 breaks after a single pinch, a flowering response of 59 to 63 days from the start of short days, and a plant height for a 6.5 inch (16.5 cm) pot of about 40–52 cm with 1–2 applications of B-9 at 2500 ppm.

1 Drawing Sheet

BACKGROUND

1. The Field of the Invention

This invention relates to Chrysanthemum plants. More particularly, the present invention comprises a new and distinct cultivar of Chrysanthemum plant, botanically known as *Dendranthema grandiflora* and hereinafter referred to by the cultivar name "Definite Eyes."

2. Background of the New Plant

Definite Eyes, identified as 87.3111, was originated from a cross made by Jack Van Der Knaap in a controlled breeding program at De Lier, Holland in 1986.

The female parent of Definite Eyes was unnamed selection #86.2409, and the male parent was unnamed selection #86.2439.

Definite Eyes was discovered and selected as one flowering plant within the progeny of the stated cross by Jack Van Der Knaap in November of 1987 in a controlled environment at De Lier, Holland.

The first asexual reproduction of Definite Eyes was accomplished when vegetative cuttings were taken in January of 1988 in a controlled environment at De Lier, Holland by technicians working under the direction and supervision of Jack Van Der Knaap.

SUMMARY OF THE INVENTION

The basic characteristics which have been repeatedly observed in Definite Eyes and which, in combination, distinguish this Chrysanthemum plant over related known varieties and its antecedents are:

1. Flat capitulum form.
2. Anemone capitulum type.
3. Pinkish white ray floret color.
4. Darker purple contrasting disc floret color.
5. Diameter across face of capitulum 4.0–7.0 cm.
6. Branching pattern is upright to spreading with ca. 3–5 breaks after a single pinch.
7. Flowering response is 59 to 63 days from the start of short days.

8. Plant height of a 6.5 inch (16.5 cm) pot is about 40–52 cm with 1–2 applications of B-9 at 2500 ppm.

Horticultural examination of controlled flowerings of successive plantings has shown that the combination of characteristics and distinctions as herein disclosed for Definite Eyes are firmly fixed and are retained through successive generations of asexual reproduction.

DETAILED DESCRIPTION OF THE NEW PLANT

Figure 1:
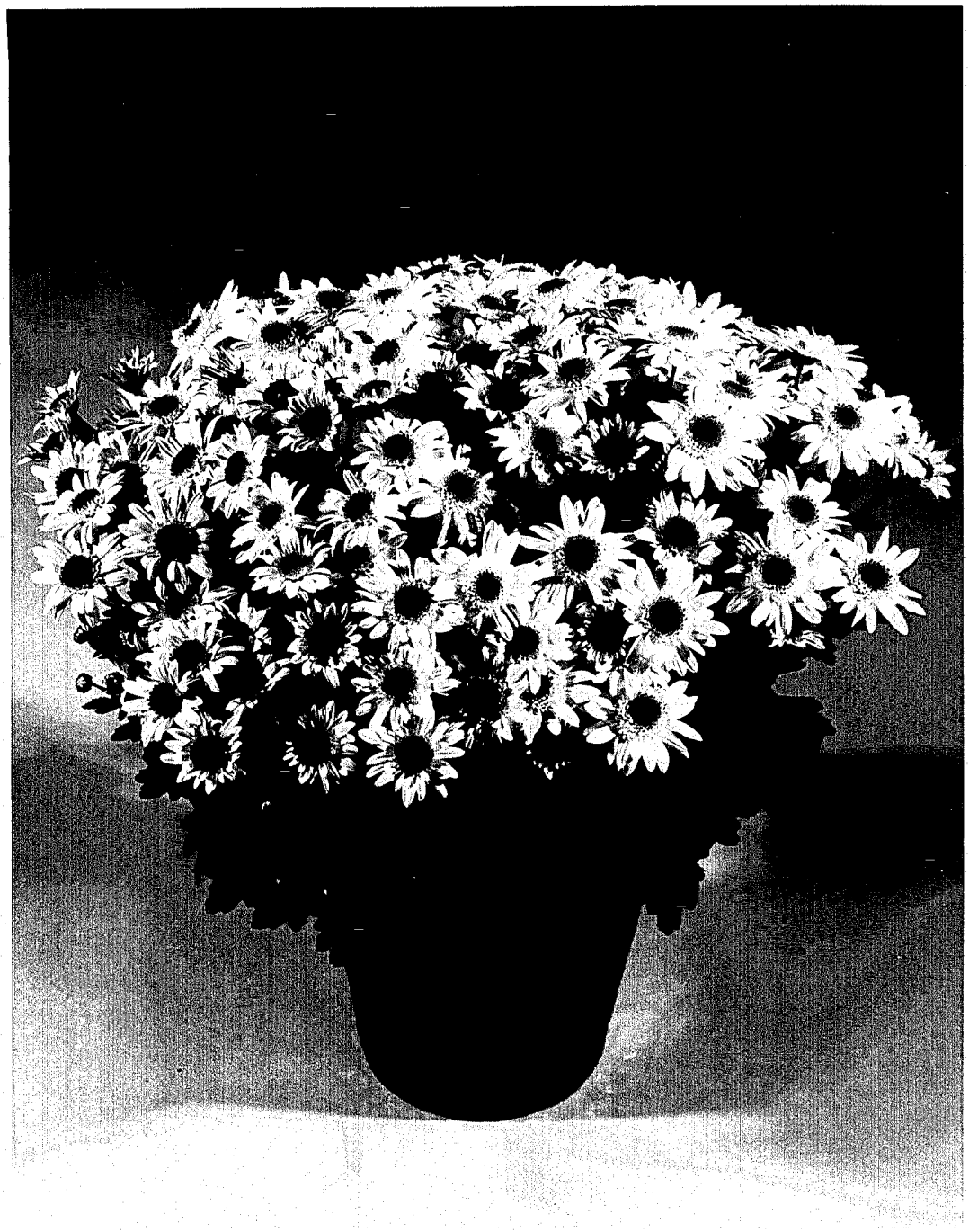
FIG. 1 is a photographic print in full color showing typical inflorescence and leaf characteristics of Definite Eyes grown as a pinched spray pot mum with 5 cuttings in a 6.5 inch (16.5 cm) pot, the colors being depicted as nearly true as it is reasonably possible to make the same in a color photograph of this character.

Definite Eyes has not been observed under all possible environmental conditions. The phenotype may vary significantly with variations in environment such as temperature, light intensity, and day length.

The following is a detailed description of Definite Eyes, with color terminology in accordance with *The Royal Horticultural Society Colour Chart*, except where general color terms of ordinary dictionary significance are obvious. The following observations, measurements and comparisons were made of plants grown at Nipomo, Calif. in controlled environments. Unrooted cuttings were directly stuck into 6.5 inch (16.5 cm) pots and grown in a controlled environment under the natural temperature and day length prevailing during October to December of 1990.

Classification:

*Botanical*.—*Dendranthema grandiflora* cv. Definite Eyes.

*Commercial*.—Flat anemone to be grown as a spray pot.

INFLORESCENCE

A. Capitulum:

*Form.*—Flat.

*Type.*—Anemone.

*Diameter across face.*—40–70 mm when fully opened.

B. Corolla of ray florets:

*Color (general tonality from a distance of three meters).*—Pale pink graduating to a dark purple eye.

*Color.*—Front: 69 D. Back: some 70 C.

*Shape.*—Elliptic.

C. Corolla of disc florets:

*Color.*—The center of the cushion is dark maroon 59A, and the other rows of the cushion are a much lighter 56C.

D. Reproductive organs:

*Androecium.*—Present on disc florets only; insignificant.

*Gynoecium.*—Present on both ray and disc florets; insignificant.

PLANT

A. General appearance:

*Height.*—When grown in 6.5 in. (16.5 cm) pots with 1–2 applications of B-9, the total plant height including the pot will be 40–52 cm.

*Branching pattern.*—Upright to spreading with 3–5 breaks after the pinch.

B. Foliage:

*Color (upper surface).*—147 A.

*Color (lower surface).*—147 B.

*Shape.*—See FIG. 1. Up to 6 cm long. Up to 4 cm wide.

Definite Eyes can be well distinguished from other commercial Chrysanthemum cultivars, including Autumn Eyes (U.S. Plant patent application Ser. No. 712,334, filed Jun. 7, 1991), Dark Eyes (U.S. Plant patent application Ser. No. 712,903, filed Jun. 7, 1991), Quiet Eyes (U.S. Plant patent application Ser. No. 712,052, filed Jun. 7, 1991), Tara (U.S. Plant Pat. No. 6,313), and Vibrant Eyes (U.S. Plant patent application Ser. No. 712,901, filed Jun. 7, 1991). See in this regard the data presented in Table A hereafter. Also, the blossom coloration of Definite Eyes can be readily distinguished from Cherub U.S. Plant Pat. No. 4,629), Rave (U.S. Plant Pat. No. 5,738), Franky Lane (U.S. Plant Pat. No. 6,302), and California Moneymaker (U.S. Plant Pat. No. 6,851) as described in the respective U.S. Plant Patents.

Similar traits to the other above-mentioned Eye varieties are capitulum form and type (with the exception of Quiet Eyes which is a flat daisy type), branching pattern, and the distinctly contrasting center of the disc. However, each Eye variety varies in color of the disc and ray florets, making each a unique and different cultivar.

Similar traits to Tara are capitulum form and type, and breaks/pinch. Definite Eyes, generally has more ray florets and more disc florets per flower, and the ray florets are generally longer by an average of 1 cm. Definite Eyes is approximatly 4–7 days slower, and has fewer flowers per break than Tara. The coloration of the petals is very different between Tara and Definite Eyes.

TABLE A

| Characteristic | Autumn Eyes | Dark Eyes | Definite Eyes |
|---|---|---|---|
| capitulum form | flat | flat | flat |
| capitulum type | anemone | anemone | anemone |
| diameter across face | ca. 3.4 cm | ca. 3.5–6.0 cm | 4.0–7.0 cm |
| branching pattern | upright | spreading | upright and spreading |
| breaks/pinch | ca. 4.0 | 4–7 | 3–5 |
| height in 6.5 in. (16.5 cm) pot with 1–2 applications of B-9 | 30–40 cm | ca. 40 cm | 40–52 cm |
| disc floret color | golden 11 A tipped with dark maroon 59 A; eye is dark maroon 59 A | medium lavender 75 C graduating to a very dark eye of 77 A; tube 75 C | 56 C on the outer petals graduating to a dark purple eye of 59 A |
| no. disc florets | ca. 171 | ca. 145 | ca. 225 |
| length disc florets | ca. 1.0 cm long | 1.0–1.5 cm long | up to 2 cm long |
| ray floret color | front: golden yellow 11 A back: pale yellow 11 B | front: 75 C back: 75 C with a 77 B stripe down the center | front: 69 D back: some 70 C |
| no. ray florets | ca. 22 | 24–27 | average of 27.3 |
| shape ray florets | oblong with rounded to flat tip | oblong with rounded tip | elliptic |
| length ray florets | 1.0–1.5 cm long | up to 2.5 cm long | up to 4 cm long |
| width ray florets | 0.3–0.5 cm wide | up to 0.75 cm wide | up to 1.0 cm wide |
| no. flowers/break | ca. 9.6 | average of 5.16 | average of 5.3 |
| leaf color | front: 147 A back: 147 B | front: 147 A back: 147 B | front: 147 A back: 147 B |
| leaf length | ca. 7.5 cm long | up to 8 cm long | up to 6 cm long |
| leaf width | ca. 5.0 cm wide | up to 4.5 cm wide | up to 4 cm wide |
| response time | 8.5 weeks | 8.5 weeks | 8.5 weeks |

| Characteristic | Quiet Eyes | Tara | Vibrant Eyes |
|---|---|---|---|
| capitulum form | flat | flat | flat fresh; puffy rounded old |
| capitulum type | daisy | anemone | anemone |
| diameter across face | 8–10 cm | 5.0–6.5 cm | 3–4 cm |
| branching pattern | spreading | spreading | upright to spreading |
| breaks/pinch | 3–4 | 3–5 | 4–5 |
| height in 6.5 in. (16.5 cm) pot with 1–2 applications of B-9 | ca. 40 cm | ca. 37 cm | 42–52 cm |
| disc floret color | lemon yellow 1 A graduating to a large green eye of 143 A | lemon yellow 10 A | from 155 D graduating toward a dark purple eye of 77 A |
| no. disc florets | ca. 200 | 70–120 | ca. 125 |
| length disc florets | 1.3 cm long | up to 1.5 cm long | ca. 1 cm long |
| ray floret color | front: 75 B back: 75 D | front: 155 A back: 155 D | light pink to white; front: 155 A back: 155 B bright green ovary |
| no. ray | 20–24 | 15–17 | ca. 22 |

TABLE A-continued

| Characteristic | Autumn Eyes | Dark Eyes | Definite Eyes |
|---|---|---|---|
| florets | | | |
| shape ray florets | oblong | elliptic | oval with rounded tip |
| length ray florets | up to 4 cm long | up to 3 cm long | up to 1.7 cm long |
| width ray florets | up to 1.5 cm wide | up to 1 cm wide | up to 0.5 cm wide |
| no. flowers/ break | ca. 5.2 | ca. 11.3 | ca. 8.4 |

TABLE A-continued

| Characteristic | Autumn Eyes | Dark Eyes | Definite Eyes |
|---|---|---|---|
| leaf color | front: 147 A back: 147 B | front: 147 A back: 147 B | front: 147 A back: 147 B |
| leaf length | up to 10 cm long | up to 9 cm long | up to 5.0 cm long |
| leaf width | up to 5.5 cm wide | up to 5 cm wide | up to 3.0 cm wide |
| response time | 8.2 weeks | 8.0 weeks | 8.0 weeks |

I claim:

1. A new and distinct variety of Chrysanthemum plant, substantially as herein described and illustrated.

* * * * *